United States Patent [19]

Choay et al.

[11] 4,064,007

[45] Dec. 20, 1977

[54] PROCESS FOR OBTAINING AN ACTIVE PRODUCT FROM MAMMALIAN MACROPHAGES

[75] Inventors: Jean Choay, Paris; Paul Trolard, Ivry sur Seine; Henri Lucien Febvre, Paris, all of France

[73] Assignee: Institut National de la Sante et de la Recherche Medicale, Paris, France

[21] Appl. No.: 663,279

[22] Filed: Mar. 2, 1976

[30] Foreign Application Priority Data

Mar. 3, 1975 France .............................. 75.06604

[51] Int. Cl.$^2$ ..................... C12K 9/00; A61K 35/12
[52] U.S. Cl. ...................................... 195/1.8; 424/95
[58] Field of Search .......................... 195/1.8; 424/95

[56] References Cited

PUBLICATIONS

Willmer — Cells and Tissues in Culture- vol. 3 — (1966) pp. 324–326.

*Primary Examiner*—Sam Rosen
*Attorney, Agent, or Firm*—Browdy and Neimark

[57] ABSTRACT

Continuous cell lines of macrophages are provided by the in vitro action, on mammalian macrophages withdrawn in situ, of macrophage activating substances, which cause the removal by the macrophages of the other cells present in the cellular medium withdrawn. The macrophages thus isolated are then placed in a suitable culture medium, until the establishment of a continuous line of macrophages, then the macrophages established as a continuous line are cultured in the presence of a suitable activating substance and the supernatant liquid is collected from these cultures. This supernatant contains substances inhibiting the proliferation of the cells having a rapid rate of multiplication. This supernatant liquid is, if necessary, subjected to a purification process. The product is notably useful for inhibiting human tumor cells.

14 Claims, 1 Drawing Figure

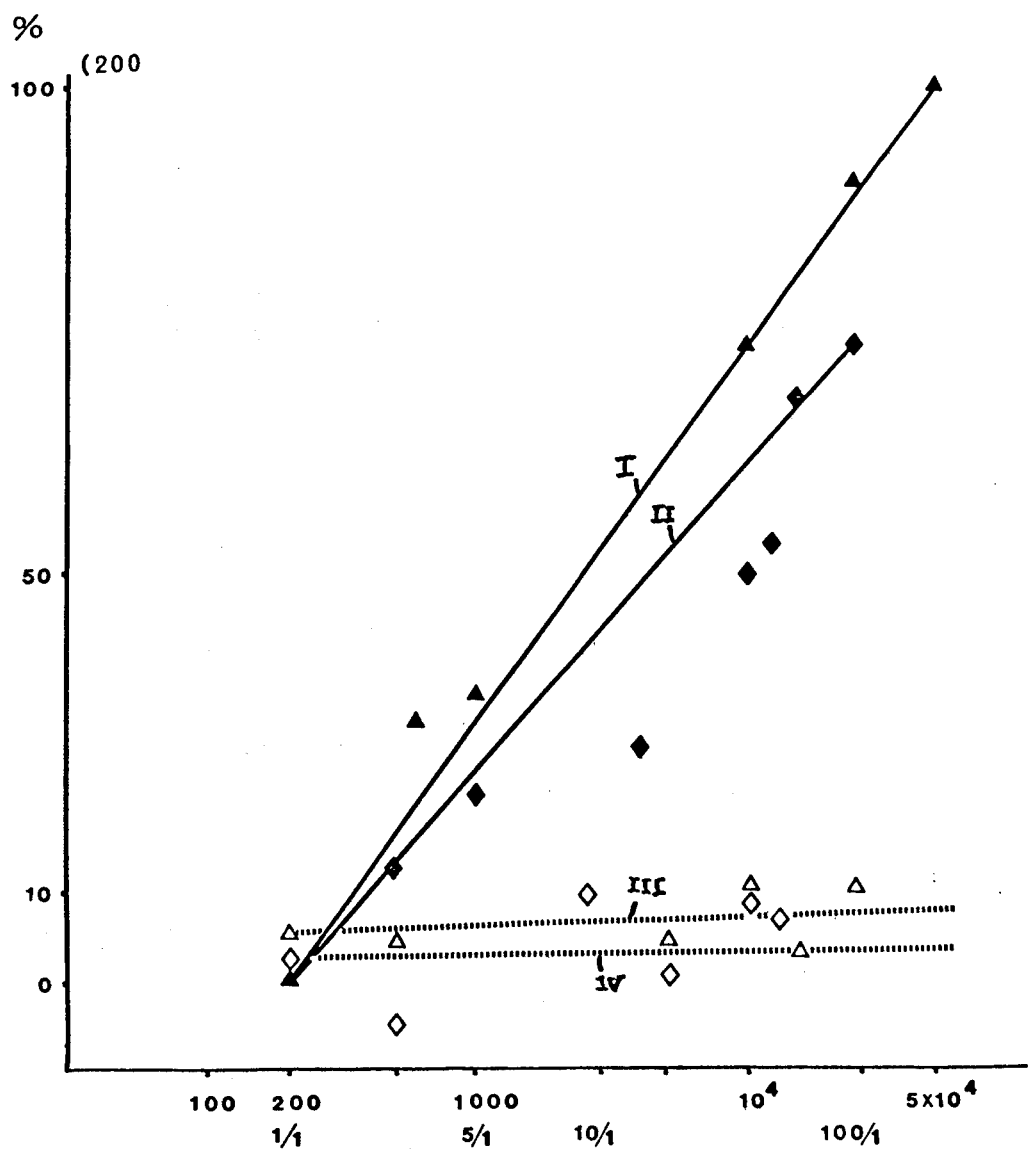

PROCESS FOR OBTAINING AN ACTIVE PRODUCT FROM MAMMALIAN MACROPHAGES

BACKGROUND OF THE INVENTION

1. Field of the Invention

The present invention relates to a process for obtaining, from mammalian macrophages, a therapeutic product, active, notably, with respect to human tumor cells, and to the therapeutic product thus obtained.

As is known, the macrophages are, either tissular histiocytes, or circulating monocytes, movable cells in the reticulo-endothelial system. They are cells of large size, 15 to 30 microns, having a nucleus with a regular structure and a weakly basophilic cytoplasm. These cells have a great tendency to macrophagia and act either by direct macrophagia, for example on bacteria, or by contact cytotoxicity, in the absence of complement.

2. Description of the Prior Art

Research investigations have established that, under certain conditions, macrophages taken from animals, in particular from rodents, exert a cytotoxic effect on tumor cells of animal origin (for example, the researches of Evans and Alexander, Nature, 236, 1972, pp. 169-171 and R. Keller, J. of Exp. Med. Vol. 138, 1973, pp. 625-644). According to the prior researches, the macrophages exert their destructive action on tumor cells either by themselves, or through their supernatant liquids (J. Galderon, R. T. Williams and E. R. Unanue, Proc. Nat. Acad. Sci. USA., Vol. 71, No 11, pp. 4273-4277, November 1974), after having been activated in vivo, that is to say, taken from animals which have previously received an injection of inflammatory agents.

All this research has the common drawback of providing experimental systems which make use of macrophages kept alive, that is to say these researches describe results obtained by means of a temporarily existing system and, if such research has established scientific results, it does not however enable a product endowed with therapeutic activity to be obtained, the raw material applied being devoid of permanence.

OBJECTS AND SUMMARY OF THE INVENTION

It is therefore an object of the present invention to provide a process for obtaining, from mammalian macrophages, a therapeutic product active, notably, with regard to human tumor cells.

It is another object of the invention to provide a therapeutic product which responds better to the requirements of practice than prior art materials.

It is also an object to provide a process and a therapeutic product whose activity has been checked by suitable studies and which is obtained from a raw material established in a permanent manner which has enabled the development of a process of preparation which is reproducable on the industrial scale.

According to the invention there is provided a process for obtaining, from mammalian macrophages, a therapeutic product active, notably, with respect to human tumor cells, characterised by the establishment of continuous lines of macrophages, by the in vitro action on mammalian macrophages swabbed in situ, of macrophage activating substances, which cause the elimination by the macrophages of other cells present in the swabbed cellular medium, then by the placing of the macrophages thus isolated in a suitable culture medium, until the establishment of a continuous line of macrophages, then by the cultivation of the macrophages established as a continuous line in the presence of a suitable activating substance, and by collecting the supernatant liquid from these cultures, which supernatant contains substances inhibiting the proliferation of the cells having rapid multiplication, and which supernatant is endowed with therapeutic activity, and which supernatant liquid is if necessary subjected to a purification process.

It was considered impossible, hitherto, to establish direct linear breeds of macrophages by reason of the fact that these cells are usually withdrawn conjointly with other cellular types, from which it was considered difficult to isolate them. In addition, one of the characteristics of the macrophages residing in adherence to their supports, (surfaces of glass or plastics material, for example), it was considered impossible, until now, to detach them from such support without injuring them, to place them in cultivation. Lastly it was considered until now that macrophages do not multiply in vitro.

According to the invention, the macrophages isolated selectively from the other cells present in the medium, by means of an activating substance, are made easy to detach from the support, such as a culture flask or the like, to which they adhere, by subjecting them to the combined effect of trypsin and of an agent chelating $Ca^{++}$ and $Mg^{++}$ ions which are the origin of the adherence of the macrophages to their support.

According to the invention, the treatment of trypsinisation and of chelation of the $Ca^{++}$ and $Mg^{++}$ ions is preceded by a first trypsinisation operation when the cellular substrate requires it.

According to an advantageous feature of the invention, the macrophages are established in continuous lines successive subcultures associated with a reactivation process by the introduction of fresh amounts of activator in the course of at least one of the successive subcultures.

In a preferred embodiment of the process according to the present invention, the mammalian macrophages, which it is sought to establish in continuous lines, are obtained from swabs at the sites where they are present in high concentrations, notably from swabs of tumors, of ascites liquids, or from embryonic organs, for example.

In a particularly preferred embodiment of the process according to the present invention, the macrophages, which it is sought to establish in continuous lines, are obtained from swabs of human origin, notably from tumor swabs of surgical origin, or from human tumoral ascites liquids or even from embryonic organs of human foeti.

According to the invention, the activating substance applied to produce the selective isolation of the macrophages from the cellular swabs medium, and the activator applied in the cultivation of cells established as a continuous line, for the obtaining of the therapeutically active supernatant liquid, may be identical or different and are selected from among macrophage activators.

The terms "activating substance" and "activator" have, within the field of the present invention, an equivalent significance.

For the application of the novel process for obtaining, from mammalian microphages, a product active, notably, with respect to tumor cells, according to the invention, the operations are preferably carried out under the conditions described below:

I. Initiation of cultivation

Mammalian macrophages, in particular human macrophages, obtained from swabs taken off from an animal, and preferably from a man, at sites where they are present in high concentrations and where they are accessible, for example from tumor swabs, from ascites liquids or from embryonic organs, are placed in cultivation in a suitable medium such as RPMI 1640, supplemented with a macrophage activator, and also advantageously supplemented with foetal calf serum, in flat bottomed flasks of plastic material, at the temperature of 37° C.

The activator is selected from among known activators of macrophages. It can be, notably, tumoral ascites liquid, bicatenary polynucleotides, mycobacteria or corynebacteria or their fractions, B or T limphocytes cultures or supernatant liquid from lymphocytes cultures for example.

It is introduced into the medium in the proportion of 5 to 20% by volume of the latter.

The foetal calf's serum is introduced in the proportion of 0 to 10% by volume of the medium.

Once the culture are obtained, they are trypsinised to separate the macrophages adhering to the walls of the flask, from the tumoral cells and from the lymphoid cells. The trypsinisation is advantageously effected by means of a 0.25% trypsin solution.

It is then washed abundantly with medium devoid of serum, to eliminate the proteins present and preserve only the macrophages.

Following this washing, the culture is left to stand for sufficient time to enable the macrophages to develop, that is to say for about one to four weeks, changing the medium regularly according to the needs of the culture, that is to say about twice a week.

II. Establishment of continuous line

Subculture is then effected in the following way:

When the macrophages have reached confluence the cells are washed for several hours in a medium without serum, then they are subjected to the action of a dilute solution (0.02%) of EDTA, then to the action of a 0.25% trypsin solution, these two operations having respectively the purpose of eliminating the $Ca^{++}$ and $Mg^{++}$ ions which constitute the elements binding the macrophages to the surface of adhesion, and to eliminate the proteins present in the medium.

The macrophage cells can then be detached from the adhesion surface, without being injured, by effecting a light scraping.

The macrophages obtained are then counted and replaced in cultivation in the ratio of 100,000 cells per ml of medium.

This subculture is repeated every ten days, until the establishment of a stable continuous line.

It is recognized that a line is stable from the fact that it reproduces in quite identical manner under identical operational conditions (doubling of the cells every ten days) and that the macrophage cells preserve, without alteration, their specific characteristics, in the course of the successive subcultures.

The selective isolation of the macrophages initiated in the course of the first culture by the addition of the macrophage activator to the medium, is accelerated by the introduction of fresh amounts of macrophage activators in the course of the subsequent passages, such "reactivation" operations having the result of eliminating any cell other than macrophage cells.

The cells cultivated as a continuous line obtained as a result can be preserved frozen, in liquid nitrogen for example, which enables amounts of cells necessary for the production of therapeutically active supernatant liquid, to be obtained.

The criteria of identification of the macrophages are the following:

The macrophages are identified by their morphologic characteristics, which are as follows:
1. Rounded cells with a central nucleus, having an undulating membrane visible in phase contrast,
2. Phagocytosis of carbon particles (China ink),
3. Resistance to detachment by trypsinisation.

To these known identification criteria has been added a fourth criteria, which is specific to macrophages established as continuous lines obtained according to the present invention, namely:
4. Destruction of tumor cells by the macrophages established as continuous lines in the presence of an activator.

BRIEF DESCRIPTION OF THE DRAWING

In order that the invention may be more clearly understood, this identification criterion is illustrated in the accompanying drawing, which shows curves of inhibition by macrophages established in continuous lines, in the presence of suitable activators, of the formation of colonies of tumor cells, in comparison with the results obtained in the absence of an activator or in the presence of products which cannot exert an activating role.

These curves establish that the activation of macrophages by suitable activators renders them active with respect to tumor cells.

The experimental system used was as follows:

to obtain curve I:
  200 human mammary adenocarcinoma tumor cells, which were pure and cultivated as a continuous line (cells T 277)
  + macrophages in variable amounts
  + an activator constituted by tumoral ascites liquid
to obtain curve II:
  200 tumor cells as indicated above
  + macrophages in variable amounts
  + an activator constituted by another tumoral ascites liquid,
to obtain curve III:
  200 tumor cells as indicated above,
  + macrophages in variable amounts
  + non-cancerous ascites liquid
to obtain curve IV:
  200 tumor cells as indicated above
  + macrophages in variable amounts
  + foetal calf serum Although for curves I and II the proportion of inhibition was respectively 95 and 75%, for $2 \times 10^4$ macrophages, namely when the ratio between the number of macrophages and the number of tumor cells reaches 100/1, the curves III and IV show that in the absence of an activator, the formation of colonies of tumor cells is not inhibited, since the rates of inhibition obtained are, respectively, 4% for the curve III and 0% for the curve IV.

Curves I and II establish that the inhibitive effect is proportional to the amount of activated macrophages present in the culture.

Compared with curves III and IV, they establish that the inhibitive effect is optimal when the activator is constituted by tumoral ascites liquid.

III. Obtaining of Macrophage Culture Supernatant Liquid

The macrophage cells established as a continuous line and preserved frozen (under liquid nitrogen, for example) are thawed and placed in cultivation under the following conditions:

At the minimum $1 \times 10^5$ cells per ml of medium are placed in a flat-bottomed flask of plastic material of 250 ml for the time necessary for the culture to reach its confluence state at the bottom of the flask.

The culture medium is advantageously the usual RPMI 1640 medium, supplemented or not with with foetal calf serum. To this medium a macrophage activator of the type mentioned above is added. The medium is normally changed every 72 hours.

The culture is effected at the temperature of 37° C in the presence of air advantageously supplemented with about 5% of $CO_2$.

The macrophage activator applied may be identical or different from that applied for establishing the macrophages as a continuous line.

The supernatant liquid is then collected and its therapeutic activity is checked by means of activity tests of which an account will be given below.

It may be found advantageous to purify the supernatant liquid to isolate the active fraction therefrom.

In addition to the foregoing features, the invention comprises also other features, which will emerge from the description which follows.

The present invention relates particularly to the processes for obtaining from mammalian macrophages, a therapeutic product active notably with respect to human tumor cells, in accordance with the features which have been mentioned, to therapeutic products obtained by these processes, as well as the means for the rise of these processes and the applications of these therapeutic products.

DESCRIPTION OF PREFERRED EMBODIMENTS

The invention will be better understood from the more detailed description which follows, which refers to examples of the rise of the new process according to the invention.

It must be well understood, however, that these examples are given purely by way of illustration of the invention and are not to be considered as constituting in any way a limitation thereof.

EXAMPLE 1

Obtaining a product endowed with therapeutic activity, from a continuous line of macrophages established from a tumoral swab:

The swab was derived from a cerebral metastasis of a tumor of the suprarenal gland.

a. The tumor swab was cut up into small fragments and subjected to the action of a 0.25% trypsin solution, at the temperature of 37° C for a period of 30 minutes. This operation was repeated three times.

b. The trypsin solution containing the cells was centrifuged, the cells were counted and placed in cultivation in 250 ml flat-bottomed flasks of plastics material, in the proportion of $1 \times 10^7$ cells per 20 ml of medium, per flask. The medium was constituted by the RPMI 1640 medium to which 10% of foetal calf serum and 10% of macrophage activator were added; the activator used in the present Example was tumoral ascites liquid rendered acellular by centrifugation and if necessary by filtration.

The medium was changed twice weekly and, at the end of one week, there was observed in this culture, a mixture of cells of fibroblastic appearance, of cells of epithelial appearance and of round cells of macrophagic appearance.

c. First Subculture:

The medium was taken off, and was replaced by a trypin solution. The fibroblastic and epithelial cells became detached and the macrophages continued to adhere to the bottom of the flask. The trypsin solution was removed and the culture was washed by means of RPMI 1640 medium without from serum. RPMI 1640 medium supplemented with serum and activator was then introduced under the same conditions as previously, on the cells which continued to adhere to the bottom of the flask. Cultivation was again maintained, changing the medium twice weekly, until confluence of the cells on the bottom of flask. At the end of this time, about 1 to 4 weeks, it was observed again that tumoral cells of the epithelial type were present; these were removed under the same conditions as above, that is to say by the addition of a macrophage activator, trypsination and washing.

d. Second Subculture and Following Subcultures

When the tumoral cells and the fibroblasts had disappeared, the macrophages were detached by chelation and trypsinisation followed by slight scraping. The operation was repeated four times until the obtaining of a pure macrophage culture as a continuous line identified as M 249 line and deposited in the American Type Culture Collection Repository under Number CL 178. The line thus obtained was preserved frozen in liquid nitrogen.

e. Cells established as a continuous line as has just been described, and preserved in liquid nitrogen, were thawed and placed in cultivation under the following conditions:

$1 \times 10^6$ cells were placed in a Petri dish of plastics material 10 cm in diameter with a flat bottom, containing 10 ml of RPMI 1640 medium supplemented with 10% of foetal calf serum and 10% of tumoral ascites liquid.

The culture was continued for about 72 hours at 37° C in an incubator supplied with air supplemented with 5% of $CO_2$. The supernatant liquid from this culture was collected at the end of 72 hours and its therapeutic activity was checked by means of tests which will be described below.

EXAMPLE 2

Obtaining of a product endowed with therapeutic activity from a continuous line of macrophages established from a swab of human tumoral ascites of ovarian origin.

a. The ascites liquid taken under sterile conditions was centrifuged at 2000 revolutions/minute for 20 minutes. The liquid was decanted under sterile conditions. The cells in the solid residue were counted and resuspended in the ratio of 17 cells in 20 ml of RPMI 1640 culture medium supplemented with 10% of foetal calf serum, and placed in cultivation in 250 ml flat bottomed flasks of plastics material.

Cultivation was maintained for 8 days, with change of the medium as necessary.

At the end of 8 days, the presence in this culture of a mixture of tumoral cells of epithelial appearance and of macrophages, was observed.

b. The tumoral cells were removed by trypsinisation as described in (c) of Example 1 above and the detachment of the macrophages from the walls of the flask was facilitated, as described in Example 1, by the addition of a chelating agent for the Ca++, Mg++ ions and of trypsin, followed by slight scraping which caused the detachment of the macrophages from the walls to which they were adhering.

The culture was maintained under the same conditions as in Example 1, with change of the medium according to needs.

At the end of 8 days, the almost total disappearance of the tumoral cells was noted; the subsisting tumoral cells were removed by trypsinisation, action of a chelating agent and washing.

The operation of subculture was repeated three times and a pure culture of macrophages established as a continuous line was obtained, which was preserved frozen under liquid nitrogen; said line, identified as M 511 line, has been deposited in the American Type Culture Collection Repository under Number CL 181.

c. The obtaining of the supernatant macrophage culture liquid was effected as described in Example 1, (e), using however as an activator Poly I:C, instead of ascites liquid.

EXAMPLE 3

Production of a product endowed with therapeutic activity from a continuous line of macrophages established from human embryonic organs.

a. The raw material is human foetal kidneys which are cut up into small fragments and then subjected to the action of an 0.25% trypsin solution, at 37° C, for 30 minutes, to liberate the cells.

This operation is repeated three times.

b. The trypsin solution containing the cells is centrifuged, then the cells are placed in cultivation as described in b) of Example 1, by adding however to the RPMI 1640 medium, 20% of calf serum and 2 ml of a solution containing 2 mg/ml of sterile Poly I:C.

c. and d. The subculture operations are carried out by proceding as described in Example 1, and e. the therapeutically active supernatant liquid is obtained by using as activator a fraction of mycobacteria such as killed BCG present at a concentration of 2 mg/ml.

EXAMPLE 4

Production of a product endowed with therapeutic activity from a continuous line of macrophages established from human embryonic organs.

The process was as described in Example 3 above, except that at stage (e) the activator used was supernatant liquid from B and T lymphocytes cultures, at a concentration of 10%.

EXAMPLE 5

Production of a product endowed with therapeutic activity from a continuous line of macrophages established from human embryonic organs.

The procedure was as described in Example 3 above, except that at state (e) the macrophage activator used was mixed cultures of B and T lymphocytes in lines, supplemented in the proportion of $1 \times 10^6$ lymphocytic cells per $1 \times 10^6$ macrophages.

The therapeutic activity of the supernatant liquids obtained was checked on the basis of pharmacological experiments of which an account is given below.

The supernatant liquids obtained according to the present invention were tested for their action on two lines of human tumor cells obtained by applying the process which is the subject of the U.S. Patent application Ser. No. 560 241 filed on Mar. 20, 1975, now U.S. Pat. No. 4,017,361, in the name of Henri Lucien FEBVRE and assigned to CHOAY S.A., for : "Process for obtaining continous lines of tumoral cells in vitro", namely of the two following lines, both of which have been deposited in the American Type Culture Collection Repository respectively under Number CL 180 and CL 179:

Cell line T 277 : human mammary carcinoma,

Cell line T 249 : suprarenal carcinoma derived from the same donor as the macrophages established as continuous line M 249.

1. Inhibition of the Formation of Colonies in Vitro

The experimental pattern consists of depositing on a plastic macroplate having six wells of 2.5 cm diameter each, 200 target tumor cells in each well.

1. in the presence of the supernatant liquid to be tested in three wells,
2. and of an inert control medium in the three other wells.

The result obtained is given in Table I below in percentages, by comparing the number of colonies present in the three control cultures and in the three cultures containing the medium to be tested.

TABLE I

| Product | Number of colonies (%) | | | | Inhibition (%) |
|---|---|---|---|---|---|
| | 1st well | 2nd well | 3rd well | Average | |
| Supernatant liquid from macrophages culture + Activator (tumoral ascites liquid) | 10 | 6 | 14 | 10 | 86 |
| Controls | — | 65 | 79 | 72 | — |
| Supernatant liquid from macrophages culture without activator | 16 | 15 | 18 | 16 | 78 |
| Controls | 56 | 87 | 84 | 75 | |

It is evident from this Table that the macrophages supernatant liquid inhibits the formation of colonies, in the course of carrying out the test which has just been described.

Contrary to appearances, this result is not paradoxical, since the selective isolation of the macrophages as described in the Examples above, uses an activator, so that the macrophages are in all cases activated macrophages.

2. Inhibition of Macromolecular Synthesis Estimated by the Incorporation of Tritiated Thymidine In macroplates such as described previously, there are introduced per well of 25 mm diameter, in 1 ml of 1640 medium supplemented with 10% of embryonic calf serum (SEV):

a. either 10,000 T277 tumor cells derived from a human mammary adenocarcinoma, at the 30th subculture, b. or 10,000 human fibroblastic cells (EH20P) derived from a foetus of 4 months, at the 8th subculture.

After 24 hours of incubation at 37° C, there is added to each well 1 ml of the macrophages centrifuged culture medium, activated or not. This medium is diluted in RPMI 1640 medium supplemented with 10% SEV.

The controls were prepared with RPMI 1640 medium without macrophages culture medium; three cultures are effected for each sample to be measured: The plates are placed to incubate 24 hours, then labelled with tritiated thymidine in the following manner:

a. Labelling with ($^3$H) methyl-thymidine, 0.5 μ Curie per well for 1 hour at 37° C, in the culture medium with serum, b. Three washings with a cold buffered saline solution at pH 7.4 containing unlabelled thymidine, c. Solubilisation in 1 ml of 0.1 M NaOH d. Neutralisation and precipitation with 1 ml of 25% trichloracetic acid, e. The precipitate was collected and filtered on glass fiber filters, then washed with 10 ml of 5% trichloracetic acid and 10 ml of ethanol, f. The precipitate was solubilised in 15 ml of scintillating mixture for 12 hours, and the radioactivity was measured with a liquid scintillation counter.

The results expressed in % inhibition of the average number of signals per minute in three control cultures and three cultures placed in contact with the medium to be tested show that there is inhibition of the incorporation of $^3$H thymidine of the 277 tumor cells in contact with the supernatant liquid centrifuged and diluted to 1/4. This inhibition is very marked with the supernatant liquid of macrophages cultures placed in contact with tumor cells in the presence of the activator.

On the contrary, there is considerable stimulation of the incorporation of ADN by embryonic fibroblastic cells placed under the same conditions.

It is clear from this tolerance test that at the maximum volumes injectable in a mouse, the product according to the present invention is perfectly tolerated by the latter.

The supernatant liquid obtained by applying the features of the present invention constitute a therapeutic product of great value possessing an inhibiting activity of abnormal cellular multiplication. It constitutes also an intermediate product of great value for the production of other products endowed with therapeutic properties.

It is clear from the foregoing description that, whatever the modes of operation, embodiments and applications adopted, a new process is obtained for the production, from mammalian macrophages, of a product active, notably, with respect to tumor cells, which has the important advantage of permitting industrial production, under conditions of complate reproducability, of a medicament of great value adapted to inhibit the abnormal multiplication of cells. The product according to the present invention has in addition the advantage of constituting a valuable raw material for the preparation of other therapeutic products or for use as a laboratory reactant.

Thus, as emerges from the foregoing, the invention is in no way limited to those of its modes of application, embodiments and uses which have just been described more explicitly in the foregoing; it encompasses on the contrary all modifications which may occur to the technician skilled in the art, without departing from the scope nor from the ambit of the present invention.

I claim:

1. A process for obtaining from human macrophages, a new product inhibiting the abnormal multiplication of human tumor cells, said process comprising:

isolating macrophages by the in vitro action on human macrophages, swabbed in situ from human cells, of a macrophage activating agent which causes the removal by the macrophages of the other cells present in the swabbed cellular medium;

placing the macrophages thus isolated in a suitable culture medium until the establishment of a continuous line of macrophages;

TABLE II

INFLUENCE OF THE SUPERNATANT LIQUIDS OF MACROPHAGES CULTURES (5 × 10$^5$) ASSOCIATED OR NOT WITH T 277 CELLS (5 × 10$^4$ CELLS) ON THE ADN SYNTHESIS OF T 277 TUMOR CELLS AND OF EH20P EMBRYONIC FIBROBLASTIC CELLS (10$^3$ CELLS)

| Target cells | T 277 tumor cells | | | EH20P fibroblastic cells | | |
|---|---|---|---|---|---|---|
| | cpm | average | inhibition % | cpm | average | stimulation |
| Associated SN cultures 1) SEV Macrophages + tumor cells (16h) diluted to ¼ in the presence of : 2) | 2984 3272 2641 | 2966 ± 182 | 28% t = 4.545 p 0.005 | 983 1119 936 | 1012 ± 55 | 159% t = 11.218 p 0.05 |
| Activators (K Ascites) | 1627 1630 1507 | 1588 ± 40 | 61% t = 14.310 p 0.05 | 422 501 479 | 467 ± 23 | 20% t = 3.203 p 0.05 |
| SN of culture 1) SEV of macrophage in the presence of : 2) | 2936 3359 2922 | 3072 ± 143 | 25% t = 4.616 p 0.05 | 1451 1420 1612 | 1494 ± 59 | 283% t = 18.581 p 0.05 |
| Activators (Ascites K) | 3087 3215 3191 | 3164 ± 39 | 23% t = 5.342 p 0.05 | 381 398 438 | 406 ± 16 | 0% t = 0.916 p = NS |
| Controls Culture medium 1640 + SEV 10% | 3851 4428 4025 | 4101 ±0 171 | | 402 390 378 | 390 ± 7 | |

3. Tolerance 10 mice received 1 ml of supernatant liquid according to the invention prepared according to Example 1, in a single sub-cutaneous injection.

At the end of 10 days, all the animals were living.

culturing the macrophages established as a continuous line, in the presence of a macrophage activating agent; and collecting the supernatant liquid from these cultures, which supernatant contains substances inhibiting the proliferation of the cells having a rapid rate of multiplication.

2. Process according to claim 1, wherein the macrophages isolated selectively from the other cells present in the medium by means of an activating agent, are subjected to the combined action of trypsin and of a chelating agent for the Ca++ and Mg++ ions to thereby prevent the adherence of macrophages to support surfaces.

3. Process according to claim 2, wherein the trypsinisation and Ca++ and Mg++ chelation treatment is preceded by a preliminary trypsinisation operation.

4. Process according to claim 1, wherein the macrophages are established in continuous lines by successive subcultures using a reactivation process by the introduction of fresh amounts of activating agent in the course of at least one of the successive subcultures.

5. Process according to claim 1, wherein the activating agent applied to produce selective isolation of the macrophages from the cellular swab medium, and the activating agent applied in the culturing of the cell culture established as a continuous line to obtain the active supernatant liquid are the same.

6. Process according to claim 1, wherein the activating agent applied in the culture medium is tumoral ascites liquid.

7. Process according to claim 1, wherein the activating agent applied in the culture medium is a bicatenary polynucleotide or a mixture of bicatenary polynucleotides.

8. Process according to claim 1, wherein the activating agent applied in the culture medium comprises mycobacteria, or corynebacteria or their fractions.

9. Process according to claim 1, wherein the activating agent applied in the culture medium is a culture of lymphocytes B or T.

10. Process according to claim 1, wherein the activating agent applied in the culture medium is supernatant liquid of lymphocyte cultures.

11. Process according to claim 2, wherein the macrophages are established in continuous lines by successive subcultures using a reactivation process by the introduction of fresh amounts of activating agent in the course of at least one of the successive subcultures.

12. New product active as an agent for inhibiting the abnormal multiplication of cells, obtained by applying the process according to claim 1, which product may be used as a laboratory reagent, or as a material for preparing therapeutic products.

13. A process in accordance with claim 1 wherein the human macrophages are obtained from carcinoma tumors, from ascites liquid or from embryonic organs.

14. A process in accordance with claim 1 further comprising purifying said supernatant liquid.

* * * * *